United States Patent
Utsugi

(10) Patent No.: US 6,419,672 B1
(45) Date of Patent: Jul. 16, 2002

(54) LASER DEPILATING METHOD, SKIN HOLDING TOOL AND GLOVE AND FINGER STALL

(75) Inventor: Ryuichi Utsugi, Tokyo (JP)

(73) Assignee: DRDC Limited, Tokyo (JP)

( * ) Notice: Subject to any disclaimer, the term of this patent is extended or adjusted under 35 U.S.C. 154(b) by 0 days.

(21) Appl. No.: 09/462,395

(22) PCT Filed: May 11, 1999

(86) PCT No.: PCT/JP99/02428

§ 371 (c)(1),
(2), (4) Date: Apr. 17, 2000

(87) PCT Pub. No.: WO99/58014

PCT Pub. Date: Nov. 18, 1999

(30) Foreign Application Priority Data

May 11, 1998 (JP) .......................................... 10-127833

(51) Int. Cl.[7] .............................................. A61B 18/18
(52) U.S. Cl. ............................. 606/9; 606/131; 128/898
(58) Field of Search ................................ 606/7, 8, 9, 10, 606/13, 127, 131; 607/88–91, 93; 604/174, 176; D26/118; 128/898

(56) References Cited

U.S. PATENT DOCUMENTS

| 3,948,295 A | | 4/1976 | Lemont et al. | |
|---|---|---|---|---|
| 5,632,741 A | * | 5/1997 | Zavislan et al. | 606/9 |
| 5,722,959 A | * | 3/1998 | Bierman | 604/174 |
| 5,820,625 A | * | 10/1998 | Izawa et a. | 606/9 |
| 5,938,657 A | * | 8/1999 | Assa et al. | 606/9 |
| 5,993,439 A | * | 11/1999 | Costello et al. | 606/9 |
| 6,162,185 A | * | 12/2000 | Amano et al. | 600/557 |
| 6,228,074 B1 | * | 5/2001 | Almeida | 606/9 |

FOREIGN PATENT DOCUMENTS

| JP | A49058450 | 6/1974 |
|---|---|---|
| JP | A63211304 | 4/1988 |
| JP | A6509734 | 11/1994 |
| JP | U3036232 | 1/1997 |
| WO | WO/9308715 | 5/1993 |

* cited by examiner

Primary Examiner—Linda C. M. Dvorak
Assistant Examiner—A. Farah
(74) Attorney, Agent, or Firm—Bachman & LaPointe, P.C.

(57) ABSTRACT

A method of attaining depilation by laser beam more effectively by enabling a laser beam the output of which is repressed to an extent of avoiding exertion of an effect on the peripheral tissue to reach a depth in the approximate range of 5–6 mm from the surface of the skin. The method of depilation attains required depilation by pulling out the skin of a subject and compressing the drawn skin thereby transforming part of the skin into a flap and emitting a laser beam to the region of the skin transformed into the flap.

2 Claims, 3 Drawing Sheets

LASER DEPILATING METHOD, SKIN HOLDING TOOL AND GLOVE AND FINGER STALL

TECHNICAL FIELD

A method of cosmetic surgery, and more particularly to a technique of laser depilation for removing a hair from the skin of a subject by the exposure of the skin to a laser beam and peripheral implements therefor.

BACKGROUND ART

The laser has been finding utility in various applications and has been producing prominent results therein. In the application to the removal of creases and the removal of birthmarks, it has come to bring excellent results in the medical field and the cosmetic field. In the last few years, the technique of depilation using the laser has been reaching the stage of materialization and the range of applications of the laser in the field of cosmetics has been expanding. The treatments with the laser are performed on the basis of the common principle that the skin is irradiated with the laser of a wavelength fit for absorption exclusively by a particular substance subjected to a particular treatment.

In the case of the depilation with the laser, for example, the treatment of depilation is carried out by irradiating the skin with a laser of a wavelength fit for absorption by the color of the hair subjected to the treatment. This technique is capable of selectively rupturing both a hair embedded in the interior of the skin and the tissue giving birth to this particular hair and is at a great advantage in permitting easy and infallible depilation without requiring any more trouble than the other method of depilation.

The method of laser depilation described above, however, does not necessarily eliminate need of improvement. Specifically, since the maximum depth of reach which the laser beam is allowed to attain in the skin from the surface without affecting the surface tissue of the skin is in the approximate range of 3–5 mm, it is in fact difficult to make the laser beam reach a depth greater than this maximum. Granted that the laser beam barely reaches the depth of this order, though this laser beam may perform a satisfactory treatment on a thin hair (having the depth of hair root of 2–3 mm from the surface of the skin), it will encounter difficulty in effectively treating a thick hair (having the depth of hair root of 5–6 mm from the surface of the skin) which places a serious demand on the treatment. If the treatment is insufficient, it will possibly result in increasing the ratio of regeneration of the treated hair. The difficulty similarly arises in the removal of a crease or in the removal of a birthmark for the sake of cure. At present, it is an urgent problem to find a way of enabling the laser beam to reach a deep portion of the skin.

This invention, therefore, aims to effectuate efficiently a method for laser depilation by aforementioned method in a manner such that the laser beam used with the output thereof repressed to the extent of avoiding exertion of an adverse effect on the peripheral tissue may be enabled to reach a depth in the approximate range of 5–6 mm from the surface of the skin and also aims to provide, in addition to the technique of laser depilation, such implements as are applicable to the removal of a birthmark and the removal of a crease, i.e. the techniques which have the same problem as the aforementioned method, and capable of facilitating the treatments under discussion as well.

DISCLOSURE OF THE INVENTION

To solve the problem mentioned above, the method of this invention for laser depilation is based on a method of laser depilation resorting to exposure of the skin of a subject to a laser beam and is inteded to effect depilation by pulling out the subject's skin and compressing it thereby deforming part of the skin into a flap and irradiating the region of the skin deformed into the flap with the laser beam. In this method of laser depilation, by causing a hair embedded in the skin to be laid sideways in accordance with a very simple procedure of deforming and compressing the skin thereby transforming the relevant part of the skin into a thin flap, it is made possible to irradiate the skin with a laser beam, with the root of the hair in a deep position approximated closely to the surface of the skin. Consequently, it is made possible to have the laser beam reach the subject of treatment such as the hair root without requiring to increase the output of the laser beam and bring about the same result as when the laser beam is made to reach a deep position.

For the purpose of implementing this method, it is necessary that the skin of a subject be pulled out till part thereof forms a flap and the skin thus transformed into the flap be retained in a compressed state. This action can be readily produced by the user of the method of this invention pinching the skin in his own hand. In this case, however, the user implementing the method of depilation is preferred to wear on his person such finger sacks or glove which is impervious to the laser beam in consideration of the possibility of his hand being irradiated excessively with the laser beam. The finger sacks or the glove mentioned above can be obtained as with a rubber composition incorporating therein a substance capable of absorbing and reflecting the laser beam.

The retention of the skin can be attained not only by resorting to the "hand" as described above but also by utilizing a skin retaining device which is provided with a retaining means and adapted to permit irradiation of the skin retained in the form of a flap with the laser beam. The retaining means in this case has no particular restriction except for a requirement that it be capable of transforming the skin into a flap and compressing and meanwhile retaining the skin so transformed into the flap. It may be, therefore, constructed of something like tongs of a transparent substance pervious to the laser beam (hereinafter referred to simply as "transparent substance 38 ), something like tongs provided with an opening allowed to confront the skin transformed into a flap, or a suction pipe adapted to produce a negative pressure in the interior thereof and formed of a transparent substance. When what resembles tongs is used as the retaining means, the skin is compressed and meanwhile retained in the form of a flap by having the skin pinched between the opposite leading terminals of the retaining means. When the suction pipe having a flat generally elliptic cross section, for example, is used as the retaining means, the skin transformed into a flap inside the suction pipe is compressed and meanwhile retained by making the skin to be sucked into the suction pipe. Since the retaining means constructed as tongs or an absorption pipe is provided with an opening opposite the skin to be retained in the form of a flap or with a part formed of a transparent substance, the skin retained in the form of a flap can be freely irradiated externally with the laser beam.

Alternatively, the retaining means may be constructed by utilizing a roller which is capable of rotating. For example, the retaining means can be formed of a roller which is enabled to rotate by being connected to a driving means and a plate member separated from the roller across a minute distance and disposed parallelly to the rotational axis of the roller. Specifically, a retaining means having attached to one of the leading terminal faces of an implement shaped like tongs a roller having a rotational axis parallel to the other leading terminal face. In this retaining means, by turning the roller in the direction of rolling in the skin, the skin transformed in the form of a flap can be compressed and meanwhile pinched between the roller and the plate member. Otherwise, a retaining means can be constructed by causing a pair of rollers at least either of which is connected to a driving means to be disposed as separated from each other across a minute distance and, at the same time, enabled to have the rotational axes thereof laid parallelly to each other. Also in this case, by the rotating force of the roller, the skin is rolled in and the skin transformed in the form of a flap is pinched between the two rollers. Incidentally, in this case, by forming part of the roller or the plate member with a transparent substance, it is made possible to irradiate the skin externally with the laser beam.

Preferably, the skin retaining device mentioned above is provided at the position thereof confronting the skin retained, in the form of a flap with a laser beam emitting terminal. By combining the skin retaining device including tongs, a roller, or a suction part as a retaining means with the laser emitting terminal in one integral piece, it is made possible to carry out continuously the work of "transforming part of the skin into a flap" or "irradiating the skin transformed into a flap with the laser beam" and consequently improve the work of depilation in efficiency. More preferably, the laser emitting terminal is adapted to scan automatically the whole surface of the skin transformed into a membrane. By so doing, the work of depilation can be expected to enjoy a further improvement in efficiency. Incidentally, for the purpose of alleviating the burden on the skin of the subject, the surface of the retaining means of this invention which is fated to contact the skin is preferred to be endowed with elasticity of a fixed magnitude.

Further, in the method of depilation explained above, the reflecting member for reflecting the laser beam is preferred to be disposed behind the region of the skin transformed into a flap and enabled to use the laser beam for irradiation. Consequently, the efficiency of depilation is allowed to be further improved because the laser beam which has penetrated the skin transformed into a flap is emitted again into the interior of the skin.

Though a popular reflecting mirror is used fully satisfactorily as the reflecting member in the present case, a glove or finger sacks adapted to reflect the laser beam on the outer surface thereof proves to be convenient for a person performing the method of laser depilation when he wears them during the course of the work. When the glove or the finger sacks constructed as described above are used, it is made possible to obtain the effect produced by the reflecting member mentioned above by simply retaining the skin in the form of a flap with a hand, placing a finger behind the skin, and irradiating the skin fronting this finger with the laser beam. For the purpose of obtaining this effect, the glove is not always required to be capable of reflecting the laser beam on the whole surface thereof but is only required to be capable of reflecting the laser beam on the part of "cushion" of the finger to be used in pinching the skin. Incidentally, the reflecting member may be used as combined with the skin retaining device mentioned above in one integral piece. What is obtained by providing an emitting terminal on the inner lateral surface of a retaining means shaped like tongs and, at the same time, forming a specular surface on the inner side of the retaining means, for example, may be regarded as a combination of a reflecting member with a skin retaining device.

BEST MODE FOR EMBODYING THE INVENTION

Figure 1:
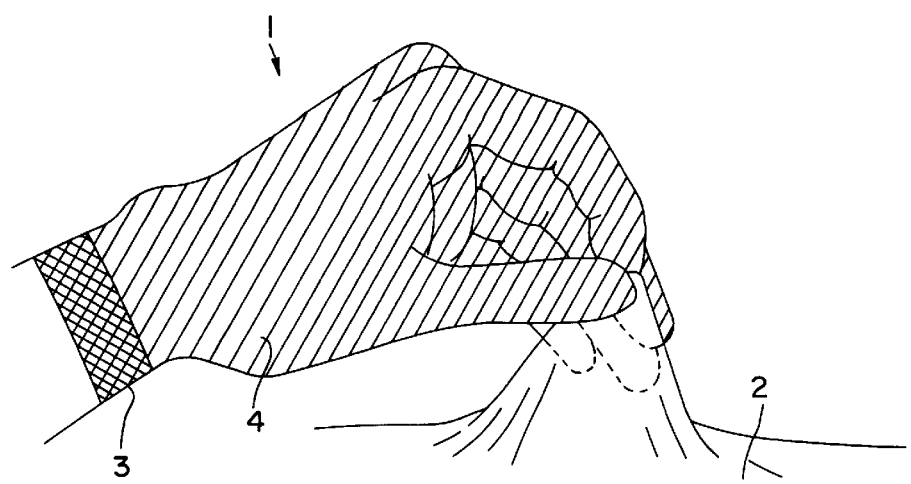
FIG. 1 is an explanatory diagram for aiding the description of one mode of embodying the method for laser depilation according to this invention.

Now, the modes of embodying the method for laser beautification according to this invention will be described below with reference to the drawings attached hereto. The reduplicating parts which occur in the following description of the modes of embodiment will be denoted respectively by identical reference numerals and will be omitted from the following description. The following description to be given below concerns the method of laser depilation. Since the removal of a birthmark with laser or the removal of a crease with laser can be effected by substantially the same method, the implements to be described hereinbelow are applicable to the method for removal of a crease or for removal of a birthmark with laser.

FIG. 1 represents one mode of embodying the method for laser depilation according to this invention. In this method, as illustrated in FIG. 1, an operator of this method is supposed to pinch a skin 2 of a subject with his own hand 1 and pull out the pinched hair 2 so as to extend part of the skin 2 in the form of a flap and then compress the skin 2 so transformed into a flap and meanwhile carry out the laser depilation. This operator wears on the hand 1 a glove 3 which is formed of a rubber composition incorporating therein a powder capable of reflecting the laser beam. To the outer surface of this glove 3 is pasted a film 4 of specular surface as a reflecting member.

When part of the skin 2 has been transformed into a flap as illustrated in FIG. 1, the region now assuming the form of a flap is irradiated with the laser beam. At this time, the laser beam is preferred to be emitted at an angle nearly perpendicular to the skin of the part transformed into the flap. The laser beam possibly penetrates the skin 2, depending on the thickness of the skin 2 transformed into the flap. When the operator places his fingers as illustrated in the diagram behind the skin 2 transformed into the flap, the laser beam which has penetrated the skin can be reflected by the specular film pasted to the surface of the glove 3 into the skin 2 transformed into the flap. The laser depilation is carried out in the manner described above.

Incidentally, in the present mode of embodiment, the glove 3 has the specular film 4 pasted to the whole outer surface thereof. So long as the specular film 4 is pasted at least to the parts of 37 cushions" of an index finger and a middle finger, it can produce an effect substantially equal to the effect mentioned above. The method of depilation mentioned above can be implemented by using a protective cover resembling finger sacks in the place of the glove 3.

Figure 2:
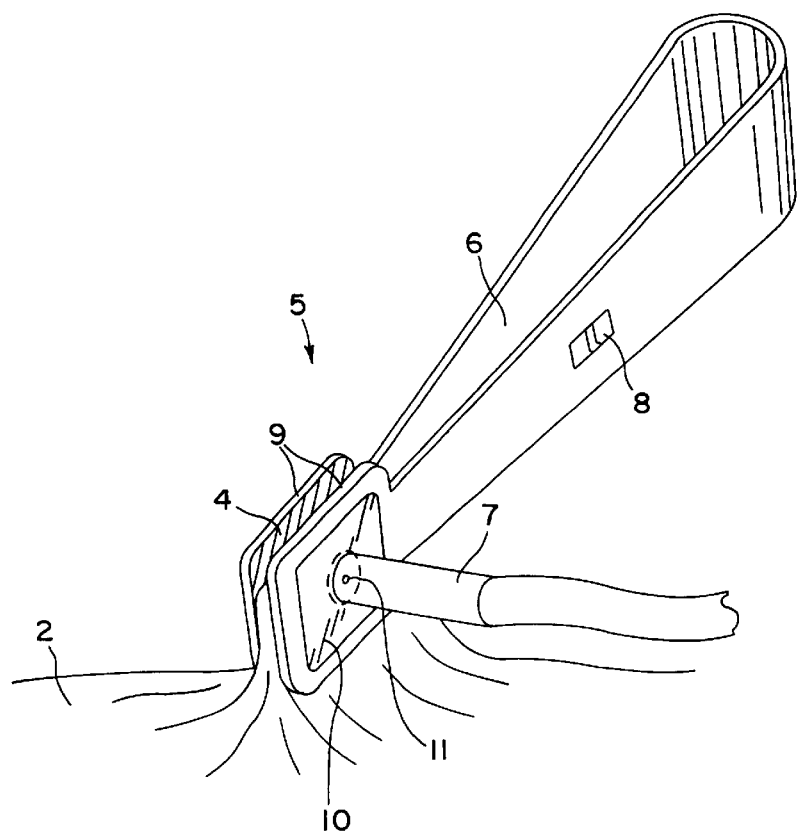
FIG. 2 is an explanatory diagram for aiding the description of another mode of embodying the method of laser depilation according to this invention.

FIG. 2 represents another mode of embodying the method of depilation according to the present invention. This method is intended to effect the art of beautification by the use of a skin retaining device 5.

This skin retaining device 5 is provided with a retaining means 6 and a hand piece 7 adapted to effect emission of laser. The retaining means 6 is shaped like tongs and is fitted in the handle part thereof with a switch 8. It is further provided at the leading terminal thereof with a retaining surface 9 of large width which is enabled by pinching and compressing the skin 2 to facilitate the retention of the skin 2 in the form of a flap. To the retaining surface 9 which confronts the inner side of the retaining means 6, the mirror 4 is pasted as a reflecting member.

The hand piece 7 is connected to a laser oscillator omitted from illustration herein and, at the same time, attached to either of the retaining means 6. The retaining surface 9 on the side allowing the attachment of the hand piece 7 is provided with a window part 10 formed of a transparent substance. An emitting terminal 11 of the hand piece 7 is adapted to advance through the window part 10 and confront the skin 2 transformed into a flap when it pinches the skin 2 against the retaining surface 9 on the inside of the retaining means 6. This hand piece 7 is enabled by an unshown scanning mechanism provided in the retaining means to scan the whole skin appearing through the window part 10. Incidentally, the laser emission is started or stopped by means of an unshown foot switch disposed beside the operator痴 foot. The scanning of the skin 2 by the laser emitting terminal 11 through the window part 10 can be carried out at an arbitrary timing by means of the switch 8 which is disposed outside the retaining means 6.

The method for laser depilation which resorts to this laser emitting device 5 is implemented as follows. Specifically, the operator of this method is enabled by pinching and compressing the skin 2 of a subject to retain part of the skin 2 in the form of a thin flap between the retaining surfaces 9. The operator, then In the ensuant state, fulfills required depilation by manipulating the switch 8 and inducing emission of the laser beam. At this time, the laser beam which has penetrated the skin 2 is reflected by the mirror disposed on the inside of the retaining surface 9 and permitted to contribute again to the treatment of depilation. Although the present mode of embodiment as described above has the hand piece 7 attached to only one terminal of the retaining means 6 shaped like tongs, it is naturally permissible to have hand pieces 7 attached one each to the opposite terminals.

EXAMPLE

Figure 3:
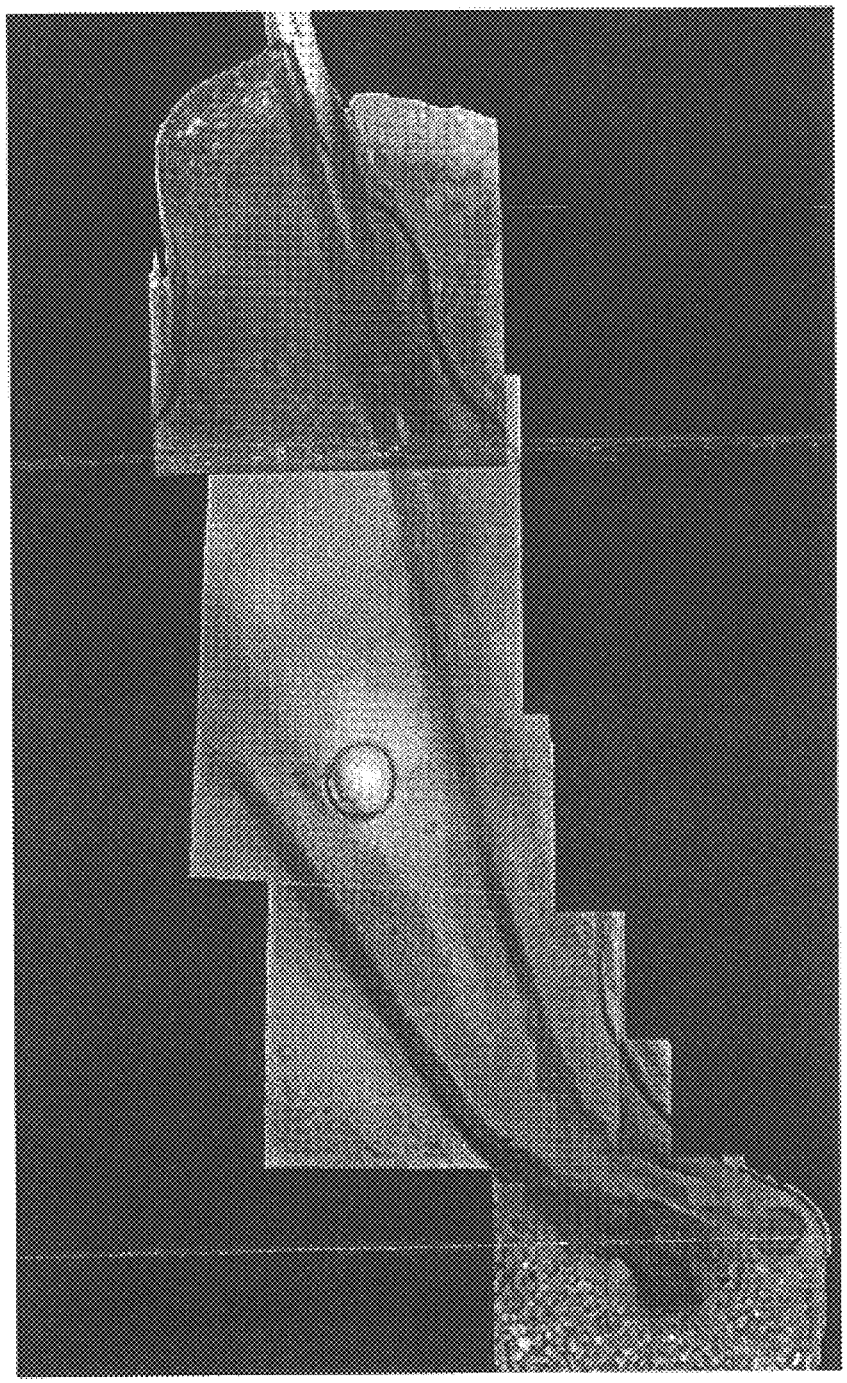
FIG. 3 is a photomacrograph illustrating the cross section of a skin which has been depilated by the method of laser depilation according to this invention.

The cross section of a skin which has undergone laser depilation by the method according to this invention (the method avoiding use of a laser emitting device) is illustrated photomacrographically in FIG. 3. It is clearly noted from this photograph that this method brings the effect of the laser beam even to a deep region of the skin and induces rupture of a hair root situated at a depth of about 6 mm from the surface of the skin.

Comparative Experiment

Figure 4:
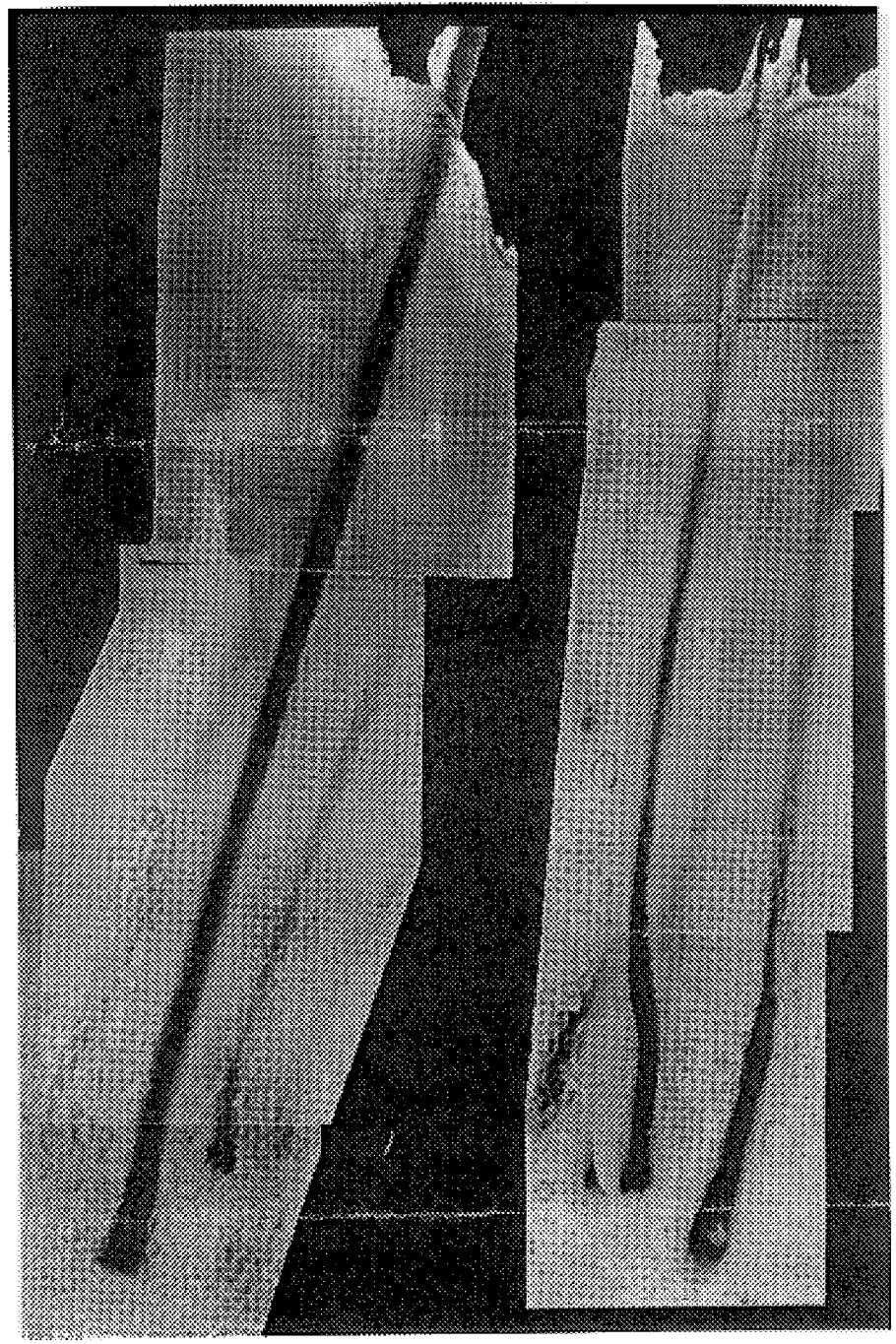
FIG. 4 is a photomacrograph illustrating the cross section of a skin which has been depilated by the conventional method.

The cross section of a skin which has undergone laser depilation by the conventional method is illustrated photomacrographically in FIG. 4. It is clearly noted from the photograph that this method brings the effect of the laser beam only to a shallow region of the skin as compared with that of FIG. 3. In the photograph of FIG. 4, the symbol (A) represents the hair prior to the treatment and the symbol (B) represents the air subsequent to the treatment.

INDUSTRIAL APPLICABILITY OF THE INVENTION

The method of laser beautification according to this invention is enabled by an extremely simple procedure of transforming part of the hair into a thin flap to emit the laser beam to the root of the hair as closely approximated to the surface of the skin. It, therefore, permits the laser beam to reach a deep position without having to use the laser bean in a high output. Further, the use of the reflecting member results in permitting utilization of the laser beam without waste and realizing highly efficient depilation. By using the glove having the outer surface thereof coated with a reflecting substance or by using the skin retaining device, it is made possible to improve the efficiency of the treatment.

What is claimed is:

1. A method for laser depilation which effects removal of a hair from the skin of a subject by exposure of said hair to a laser beam, characterized by comprising the steps of pulling out said skin of the subject and compressing the drawn skin thereby transforming part of said skin into a flap and attaining required depilation by irradiating the region of said skin transformed into said flap with said laser beam.

2. A method according to claim 1, wherein a reflecting member for reflecting said laser beam is disposed behind the region of said skin transformed into said flap prior to the emission of said laser beam.

\* \* \* \* \*